(12) United States Patent
Perrin et al.

(10) Patent No.: US 9,623,220 B2
(45) Date of Patent: Apr. 18, 2017

(54) SUTURE TRACKING DILATORS AND RELATED METHODS

(71) Applicant: ALFRED E. MANN FOUNDATION FOR SCIENTIFIC RESEARCH, Santa Clarita, CA (US)

(72) Inventors: Michael R. Perrin, West Hills, CA (US); Kenneth L. Ripley, Valencia, CA (US); Joseph L. Calderon, Culver City, CA (US)

(73) Assignee: The Alfred E. Mann Foundation For Scientific Research, Santa Clarita, CA (US)

( * ) Notice: Subject to any disclaimer, the term of this patent is extended or adjusted under 35 U.S.C. 154(b) by 191 days.

(21) Appl. No.: 14/207,404

(22) Filed: Mar. 12, 2014

(65) Prior Publication Data

US 2014/0277022 A1  Sep. 18, 2014

Related U.S. Application Data

(60) Provisional application No. 61/782,288, filed on Mar. 14, 2013.

(51) Int. Cl.
| *A61B 17/32* | (2006.01) |
| *A61M 29/00* | (2006.01) |
| *A61B 17/3209* | (2006.01) |
| *A61B 17/04* | (2006.01) |
| *A61B 17/34* | (2006.01) |
| *A61B 90/00* | (2016.01) |

(52) U.S. Cl.
CPC ......... *A61M 29/00* (2013.01); *A61B 17/3209* (2013.01); *A61B 17/3468* (2013.01); *A61B 17/0482* (2013.01); *A61B 17/0483* (2013.01); *A61B 17/3417* (2013.01); *A61B 2017/0411* (2013.01); *A61B 2090/3908* (2016.02)

(58) Field of Classification Search
CPC .............. A61M 29/00; A61B 17/3468; A61B 17/3209; A61B 2090/3908; A61B 17/3417; A61B 17/0482; A61B 2017/0411; A61B 17/0483
See application file for complete search history.

(56) References Cited

U.S. PATENT DOCUMENTS

| 6,829,508 B2 | 12/2004 | Schulman | |
| 2003/0078618 A1 | 4/2003 | Fey | |
| 2004/0127973 A1* | 7/2004 | Mangiardi et al. | 623/1.15 |
| 2004/0167572 A1* | 8/2004 | Roth et al. | 606/219 |
| 2005/0267555 A1 | 12/2005 | Marnfeldt | |
| 2006/0089646 A1* | 4/2006 | Bonutti | 606/61 |

(Continued)

*Primary Examiner* — Richard Louis
(74) *Attorney, Agent, or Firm* — Oleh J. Zajac

(57) ABSTRACT

Suture tracking dilators and methods for removing implanted medical devices such as microstimulators or microsensors from living tissue are described. A suture tracking dilator has a slit running along its axial length. The slit can have a curved portion. A suture is attached to a medical device prior to its implantation. To remove the implanted medical device, the free end of the suture is exposed and inserted in the slit in the suture tracking dilator. The suture is held under tension at its free end, the dilator is inserted in the living tissue and the dilator follows the suture to the implanted medical device. The medical device is removed by pulling on the free end of the suture.

24 Claims, 7 Drawing Sheets

(56) References Cited

U.S. PATENT DOCUMENTS

| | | |
|---|---|---|
| 2006/0178682 A1 | 8/2006 | Boehike |
| 2006/0235516 A1 | 10/2006 | Cavazzoni |
| 2006/0253181 A1 | 11/2006 | Schulman |
| 2006/0271109 A1* | 11/2006 | Kuzma et al. .................... 607/2 |
| 2007/0162051 A1 | 7/2007 | Calderon |
| 2008/0132926 A1* | 6/2008 | Eichmann .......... A61B 17/3401 606/167 |
| 2009/0043367 A1 | 2/2009 | Zilberman |
| 2009/0082788 A1* | 3/2009 | ElMaraghy ................... 606/148 |
| 2010/0023006 A1* | 1/2010 | Ellman ........................... 606/45 |
| 2010/0057176 A1* | 3/2010 | Barker .......................... 607/117 |
| 2010/0292732 A1* | 11/2010 | Hirotsuka et al. ............. 606/232 |
| 2011/0224681 A1* | 9/2011 | McDonald ......... A61B 17/3401 606/129 |
| 2012/0271323 A1* | 10/2012 | Fan et al. ...................... 606/144 |

* cited by examiner

SUTURE TRACKING DILATORS AND RELATED METHODS

RELATED APPLICATIONS

This application claims the benefit under 35 USC 119(e) of U.S. provisional patent application No. 61/782,288 which was filed on Mar. 14, 2013, and which is hereby incorporated by reference in its entirety.

FIELD OF THE INVENTION

The present invention relates to medical devices and methods. In particular, it relates to surgical suture tracking dilators and related methods, for facilitating the removal of implanted medical devices, such as microdevices.

BACKGROUND OF THE INVENTION

Microdevices are sometimes implanted in a human or animal body to perform certain functions. One such microdevice is a microstimulator, which can be implanted in a body near a nerve or muscle motor point to stimulate certain regions of the body to help patients by, for example, moving a part of their body that may otherwise be disabled. Another example of such a microdevice is an implanted microsensor, which senses a body parameter and communicates wirelessly to an external controller. A further example of an implanted microdevice is a combination microstimulator and microsensor. It is often the case that after some period of time (e.g., weeks, months or years), the microdevice is desired to be removed from the body. In such a case, an operator (e.g., doctor, nurse, or technician) finds the specific location of the implant in the body and withdraws the implanted device, either for removal or replacement.

Dilators are used by surgeons during medical procedures to penetrate and dilate body tissue, such as during the implantation or removal (explantation) of medical devices, such as microdevices into or out of an animal or human body. As part of a procedure to remove an implanted microdevice, an elongate dilator can penetrate living tissue until its distal end reaches the microdevice, and then the hollow inner portion of the dilator can provide a lumen for the passage of other surgical tools or wires to expedite the removal of the microdevice. Some microdevices are equipped with an eyelet at the proximal end, which can then be connected to a wire or other device for the removal of the microdevice. There is a need for an improved type of dilator, which can make it easier to locate and remove an implanted microdevice.

SUMMARY OF THE INVENTION

Suture tracking dilators and methods for removing implanted medical devices such as microstimulators or microsensors from living tissue are described. A suture tracking dilator has a slit running along its axial length. A suture is attached to a medical device prior to its implantation. To remove the implanted medical device, the free end of the suture is exposed and inserted in the slit in the suture tracking dilator. The suture is held under tension at its free end, the dilator is inserted in the living tissue and the dilator follows the suture up to the implanted medical device. The medical device is removed by pulling on the free end of the suture.

BRIEF DESCRIPTION OF THE DRAWINGS

Non-limiting and non-exhaustive embodiments are described with reference to the following figures, wherein like reference numerals refer to like parts throughout the various views unless otherwise specified. It should be noted that all of the apparatus figures are not drawn to scale, in order to simplify the figures.

DETAILED DESCRIPTION

In the present specification, the terms 'proximal' and 'distal' are used with reference to an operator (e.g., doctor, nurse, technician) such that a proximal side refers to the side closer to the operator and a distal side refers to the side away from the operator. For example, a blade end of a knife used by a surgeon to create an incision in a patient's body is the distal end, while a handle end held by the doctor would be the proximal end.

Figure 1:
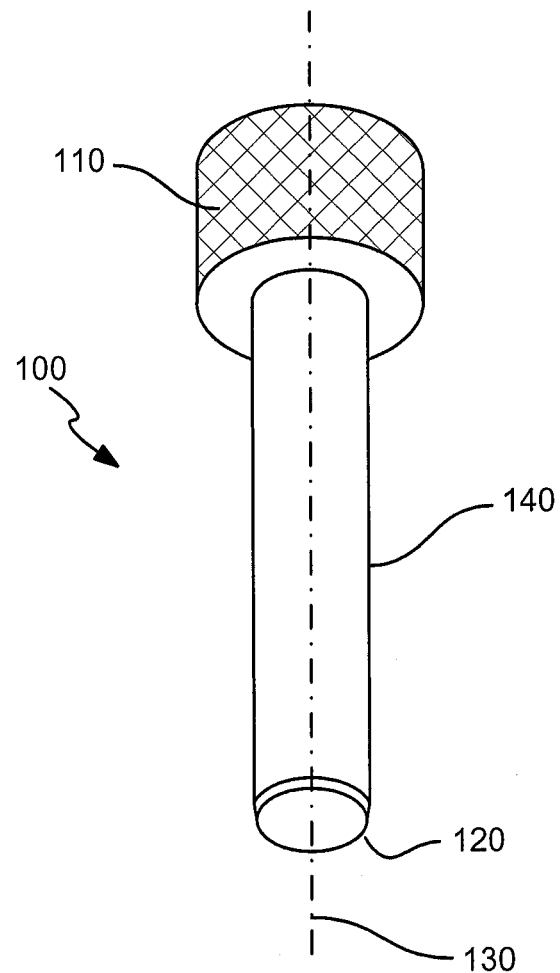
FIG. 1 is a perspective view of a prior art trephine.

A hollow cutting element, e.g., a trephine 100, as shown in FIG. 1 is a tool with a cylindrical cutting blade 120 that spins about a central axis 130 for cutting in a circular pattern during a medical procedure on a human or animal body, e.g., a surgical procedure. The trephine 100 has a tubular portion 140 on its distal end and a grip 110 portion on its proximal end. The tubular portion 140 has a hollow center, with the cylindrical cutting blade 120 located at the distal end of the tubular portion 140.

FIGS. 2A to 4B show schematic views of a functional device, e.g., a microdevice 250, implanted in the living tissue of a human or animal body and portions of a microdevice removing apparatus according to several embodiments of the present invention. The microdevice 250 can be, by way of example and not of limitation, a radio frequency powered microstimulator, a battery powered microstimulator, a microsensor or a combination microstimulator and microsensor. Examples of RF powered microstimulators are described in U.S. Pat. Nos. 5,193,539, 5,193,540, 5,312,439, 5,324,316 and 5,405,367. Examples of battery powered microstimulators are described in U.S. Pat. Nos. 6,164,284, 6,185,452, 6,208,894, 6,315,721 and 6,564,807, Examples of microsensors are described in U.S. Pat. Nos. 7,252,005 and 7,418,872. All references cited herein are incorporated by reference to the same extent as if each reference had been incorporated by reference in its entirety individually.

Figure 2A:
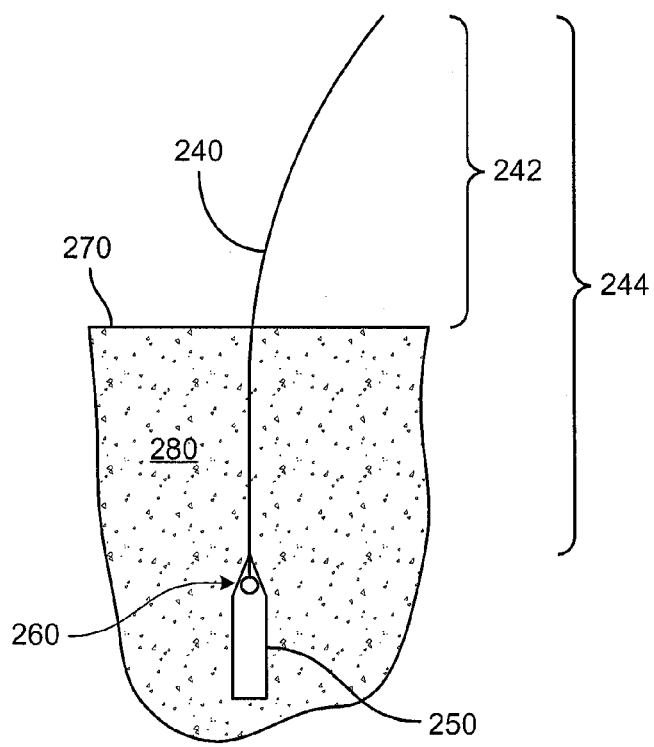
FIGS. 2A-2B are cross sectional views of a suture connected microdevice implanted in the living tissue of the body of an animal or human.
Figure 2B:
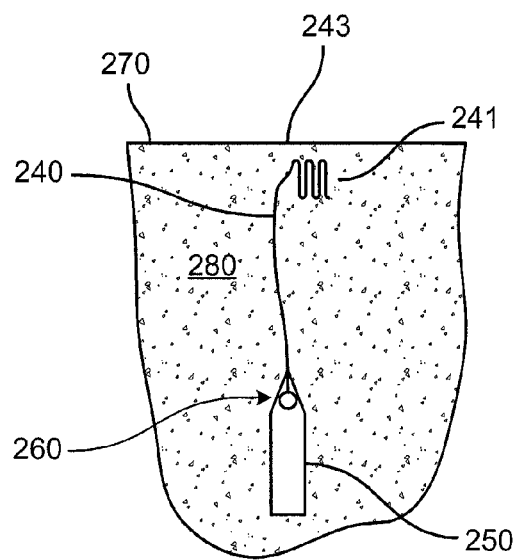

According to the embodiments shown in FIGS. 2A-2B, microdevice 250 comprises an eyelet 260 at one end to enable threading and tying on suture 240. The distal end of suture 240 had been connected to eyelet 260 before microdevice 250 was implanted below the skin 270 in living tissue 280. When microdevice 250 is implanted in living tissue 280, a certain length 244 of suture is connected to the eyelet 260 such that once the microdevice 250 is placed in a desired location inside living tissue 280, the suture extends from the eyelet 260 and protrudes a predetermined amount 242 above the skin 270. As shown in FIG. 2B, when the microdevice 250 implanting procedure is complete, the operator e.g., a doctor, tucks away the excess suture 241 at the incision point 243 through which the microdevice 250 had been inserted, underneath the skin 270. As described in the following paragraphs, the excess suture 241 can be later re-exposed from underneath the skin 270 and utilized as a guide when it is desired to remove the microdevice 250. A radio opaque suture 240 can be tied on to an implanted microdevice 250 to make it easier to locate the suture 240 on an x-ray image, which will facilitate locating the suture during removal of microdevice 250.

Figure 3A:
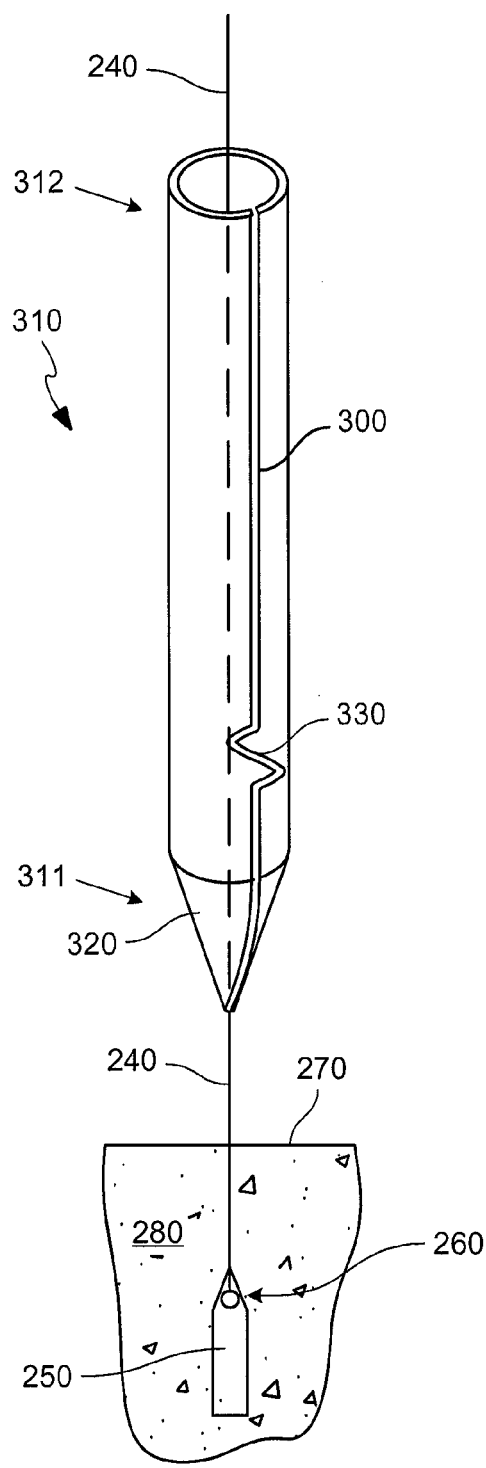
FIG. 3A is perspective view of a suture connected microdevice and a suture tracking dilator.

FIG. 3A shows a surgical device according to one embodiment of the present invention, a suture tracking dilator 310. Surgical dilators are well known surgical instruments used during surgical procedures to penetrate and dilate stiff tissue. Suture tracking dilator 310 has a cylindrical, tubular shape with a hollow core to allow for passing the suture 240 through its interior. Suture tracking dilator 310 has a slit 300, running lengthwise from the distal end 311 to the proximal end 312. Slit 300 has a curved offset 330 in proximity to the distal end 311 of dilator 310 to prevent the suture 240 from slipping out of the slit 300. The distal end 311 of suture tracking dilator 310 has a conical shape 320 which can assist in easily channeling dilator 310 through bodily tissue.

Figure 3B:
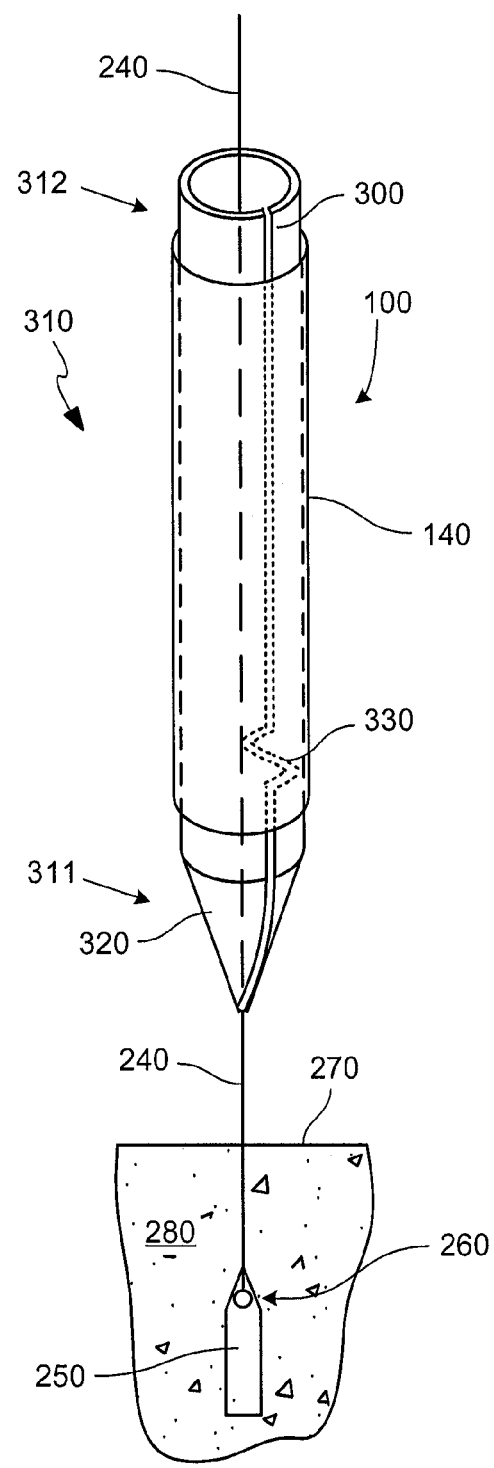
FIG. 3B is a perspective view of a suture connected microdevice and a suture tracking dilator with a trephine.

FIG. 3B shows suture tracking dilator 310, together with trephine 100, like the trephine 100 shown in FIG. 1, which has been inserted over dilator 310. For clarity of illustration, handle 110 of trephine 100 is not shown in FIG. 3B. The tubular portion 140, also having a cylindrical shape, slides snugly over suture tracking dilator 310. Slit 300 on the side of suture tracking dilator 310 has a curved offset 330, which reduces the possibility of suture 240 exiting out of dilator 310 through slit 300 during a microdevice 250 removal procedure. The snug fit of the tubular portion 140 of trephine 100 over the suture tracking dilator 310 can assist in containing suture 240 from exiting dilator 310.

Figure 3C:
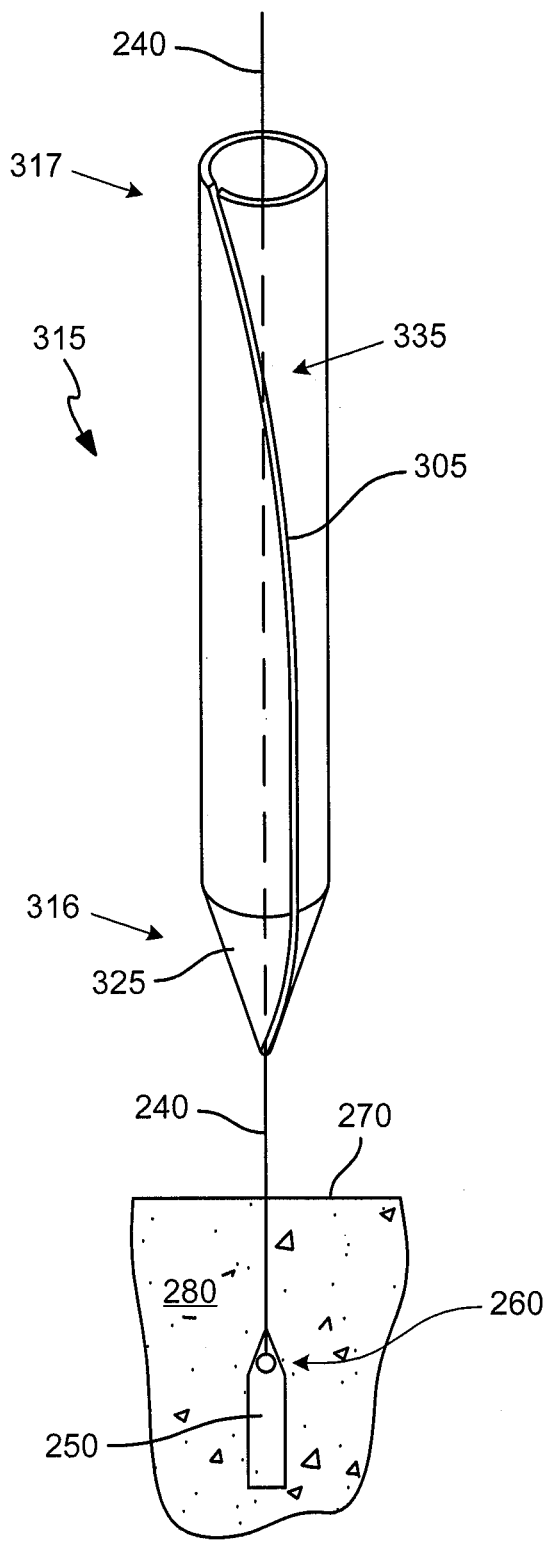
FIG. 3C is a perspective view of a suture connected microdevice and a suture tracking dilator.

FIG. 3C shows an alternate embodiment of a suture tracking dilator 315. The suture tracking dilator 315 has a cylindrical, tubular shape with a hollow core to allow for passing a suture 240 through its hollow center. The tubular portion has a slit 305, running lengthwise from the distal end 316 to the proximal end 317 of suture tracking dilator 315. Slit 305 has at least one portion 335, which is at an acute angle with respect to the horizontal central axis of dilator 315 to prevent the suture 240 from slipping out of slit 305. The distal end 316 of suture tracking dilator 315 has a conical shape 325 which can assist in easily channeling its way through bodily tissue. In other embodiments of the present invention, all of slit 305 is at an acute angle with respect to the horizontal central axis of dilator 315, i.e., there are no curved portions in such an angled slit 305.

As introduced in the previous paragraphs and in FIGS. 2A to 3C, in order to be able to remove implanted microdevice 250, a suture 240 is connected to eyelet 260 of microdevice 250, the suture 240 being a non-absorbable suture. As already shown in FIG. 2B, the suture 240 is extended to a point of entry at an incision point 243 where the microdevice 250 was initially inserted and the excess suture 241 is tucked away underneath the skin 270 until it is desired to remove microdevice 250. The non-absorbability of the suture avoids the chance of suture 240 dissolving in living tissue 280 over time.

Figure 4A:
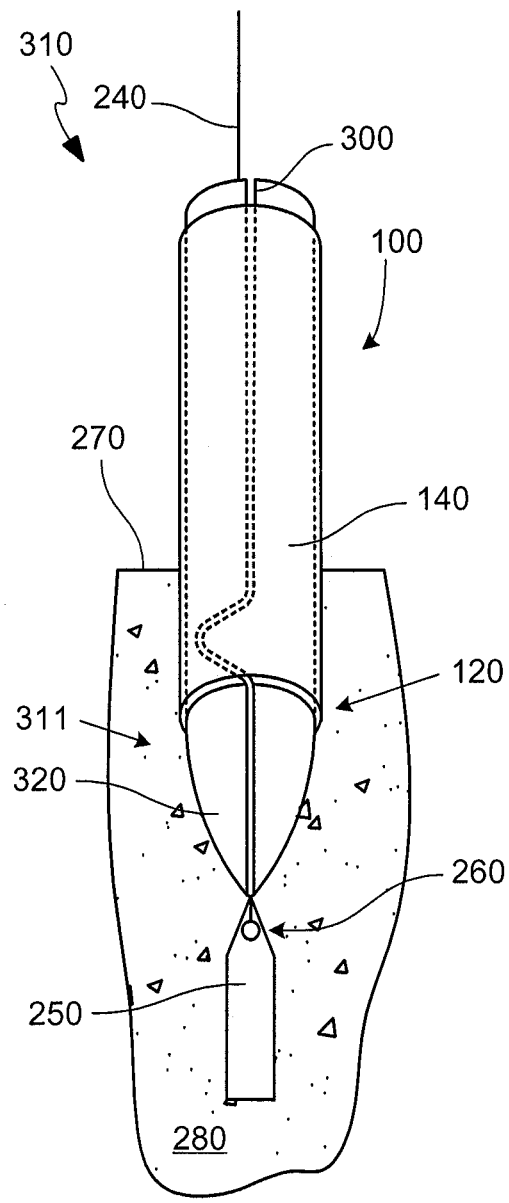
FIGS. 4A-4B are perspective views of a suture connected microdevice and a suture tracking dilator with a trephine.
Figure 4B:
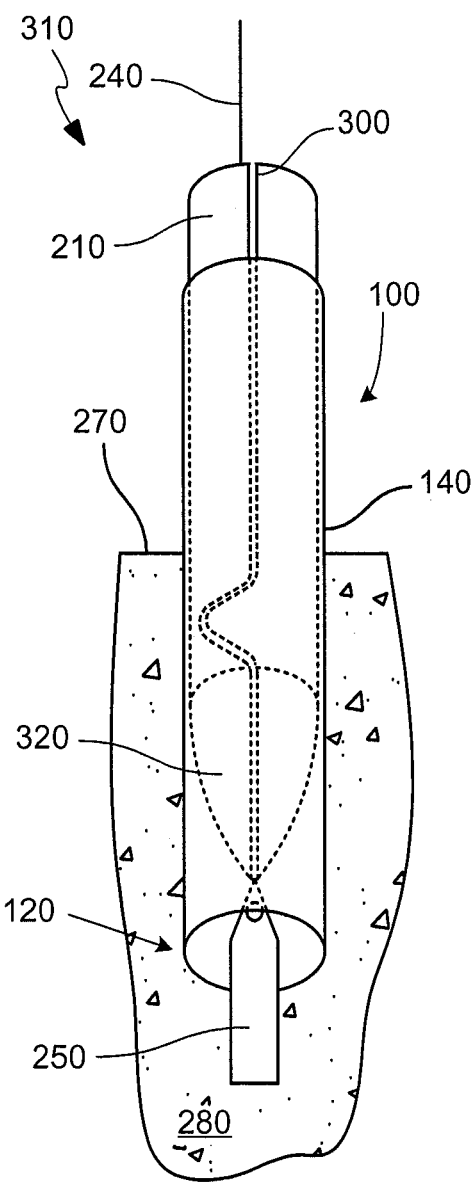

FIGS. 4A and 4B are perspective views of suture 240 connected to microdevice 250 and showing suture tracking dilator 310 with trephine tubular portion 140 during a procedure to remove microdevice 250 from living tissue 280. For clarity of illustration, handle 110 of trephine 100, as shown in FIG. 1, is not shown in FIG. 4A or FIG. 4B. As shown in FIG. 4A, the distal end 311 of suture tracking dilator 310 goes through the skin 270 with the help of cutting blade 120 of trephine tubular portion 140. In an alternate embodiment, a suture tracking dilator can go through the skin 270 without the help of cutting blade 120 of trephine tubular portion 140.

FIG. 4A shows suture tracking dilator 310 with trephine tubular portion 140 following suture 240 into living tissue 280 and the distal end 311 of dilator 310 has reached the proximal end of microdevice 250, where the conical portion 320 of dilator 310 is adjacent to eyelet 260 of microdevice 250. At the point in the procedure shown in FIG. 4A, trephine tubular portion 140 is positioned on dilator 310 but the cutting blade 120 has not yet engaged the encapsulating tissue adjacent to microdevice 250. Any one of many possible imaging methods, e.g., fluoroscopy, can be used to verify that the distal end 311 of dilator 310 has reached the proximal end of microdevice 250.

FIG. 4B shows suture tracking dilator 310 with trephine tubular portion 140 following suture 240 into living tissue 280 and trephine 100 has been pushed towards microdevice 250 by sliding over dilator 310 and has cut into the encapsulating tissue around eyelet 260 of microdevice 250. As the operator continues pushing and rotating trephine 100 over microdevice 250, eventually the trephine 100 will cut away all of the encapsulating tissue around microdevice 250 and microdevice 250 will be ready to be removed from its implantation site.

As previously noted, FIGS. 1-5 are not drawn to scale, in order to simplify the drawings. In FIGS. 3B, 4A and 4B, the diameter of microdevice 250, for example, appears to be much smaller than the inside diameter of the cylindrical portion 140 of the trephine 100, In actual practice, the inside diameter of tubular portion 140 would be not much larger than the diameter of microdevice 250, so as to enable cutting blade 120 to closely encircle microdevice 250 and minimize the cutting of tissue not in proximity to microdevice 250. Similarly, the inside diameter of the suture tracking dilator 310 shown in FIGS. 3A to 4B would be not much larger than the diameter of microdevice 250.

According to the embodiments shown in FIGS. 3A to 4B, when it is desired to remove or replace microdevice 250, the operator, e.g., a doctor, initially exposes and extends the suture 240 that was tucked away when the microdevice 250 was implanted, from underneath the skin 270 by creating a surgical incision in the proximity of the region containing the excess suture. Suture 240 is then placed inside the hollow portion of the suture tracking dilator 310 by passing the suture 240 through the slit 300. Once the suture 240 is inside dilator 310, the tubular portion 140 of trephine 100 is slid over the tubular portion of dilator 310 to a point such that the conical portion 320 of dilator 310 remains fully exposed. While ensuring that the proximal end of the suture 240 remain external to the skin 270, the operator pushes the suture tracking dilator 310, with trephine 100 around it, towards the living tissue of the patient using suture 240 as a guide.

Once the cylindrical portion 140 of trephine 100 slides over and covers microdevice 250, the microdevice 250 is free from the encapsulated tissue. Microdevice 250 can be removed by simultaneously withdrawing dilator 310, trephine 100 and suture 240. By withdrawing suture 240, microdevice 250 is also withdrawn since the distal end of suture 240 is connected to microdevice 250 by eyelet 260.

In an alternative method, microdevice 250 can be removed by first withdrawing trephine 100, followed by withdrawing simultaneously the suture tracking dilator 310 and suture 240. Again, by withdrawing the suture 240, microdevice 250 is also withdrawn since the distal end of the suture 240 is connected to microdevice 250 by eyelet 260.

Figure 5:
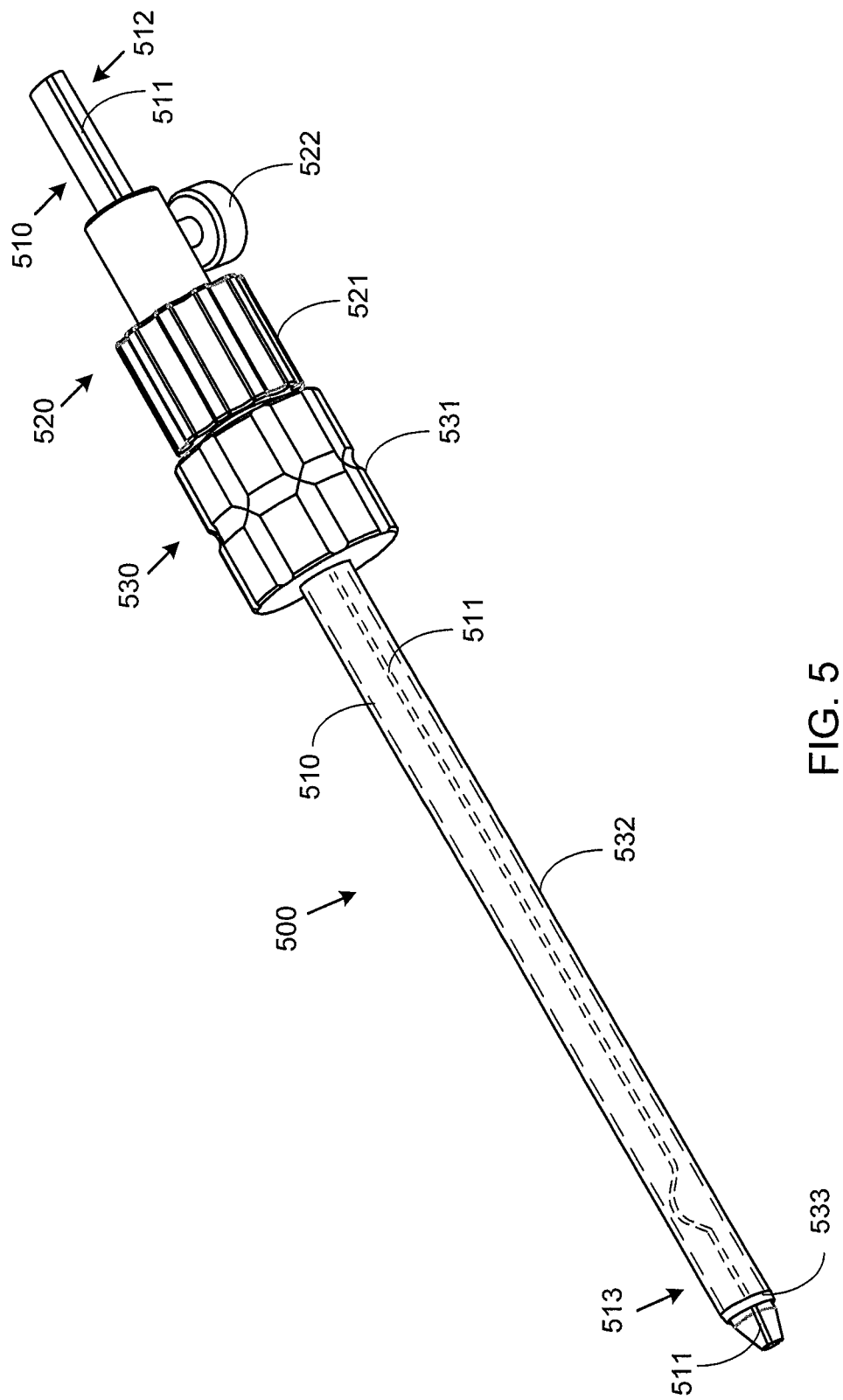
FIG. 5 shows an apparatus for removal of microdevices including a suture tracking dilator, a handle and a trephine.

FIG. 5 shows an apparatus 500 for removal of medical devices, such as microdevices, including a suture tracking dilator 510, dilator handle 520 and trephine 530. Dilator 510 includes a slit 511 at the proximal end 512, which is also seen at distal end 513. Dilator handle 520 and trephine 530 are slid over dilator 510 during a microdevice removal process. Handle 520 includes grip 521 with thumbscrew 522 used to fasten handle 520 onto dilator 510. Grip 521 can be used to hold apparatus 500, and can also be a sleeve for a threaded coupling such as a female Luer lock connector. Thumbscrew 522 is an exemplary way of fastening or locking handle 520 to dilator 510. Trephine 530 includes grip 531, tubular portion 532 and cylindrical cutting blade 533. Grip 531 can be used to hold trephine 530, and can also be a tabbed hub for a threaded coupling such as a male Luer lock connector. When grips 521 and 531 incorporate compatible couplings that lock together, then they can be used to releasably couple handle 520 and trephine 530. When handle 520 is fastened to dilator 510 and grips 521 and 531 are coupled together, the combined grip made of 521 and 531 provides a larger gripping surface for a surgeon during the process of following a suture 240 and inserting dilator 510 into living tissue. A larger grip on apparatus 500 enables a surgeon to more easily hold dilator 510 and apply the requisite force needed to push dilator 510 into living tissue.

In an alternate embodiment of the present invention, an apparatus (not shown) similar to apparatus 500 in FIG. 5 includes a trephine with a handle similar to the one shown in FIG. 1, where the trephine can be locked to a suture tracking dilator, such as dilator 510, with a mechanism, such as thumbscrew 522 shown in FIG. 5.

Figure 6:
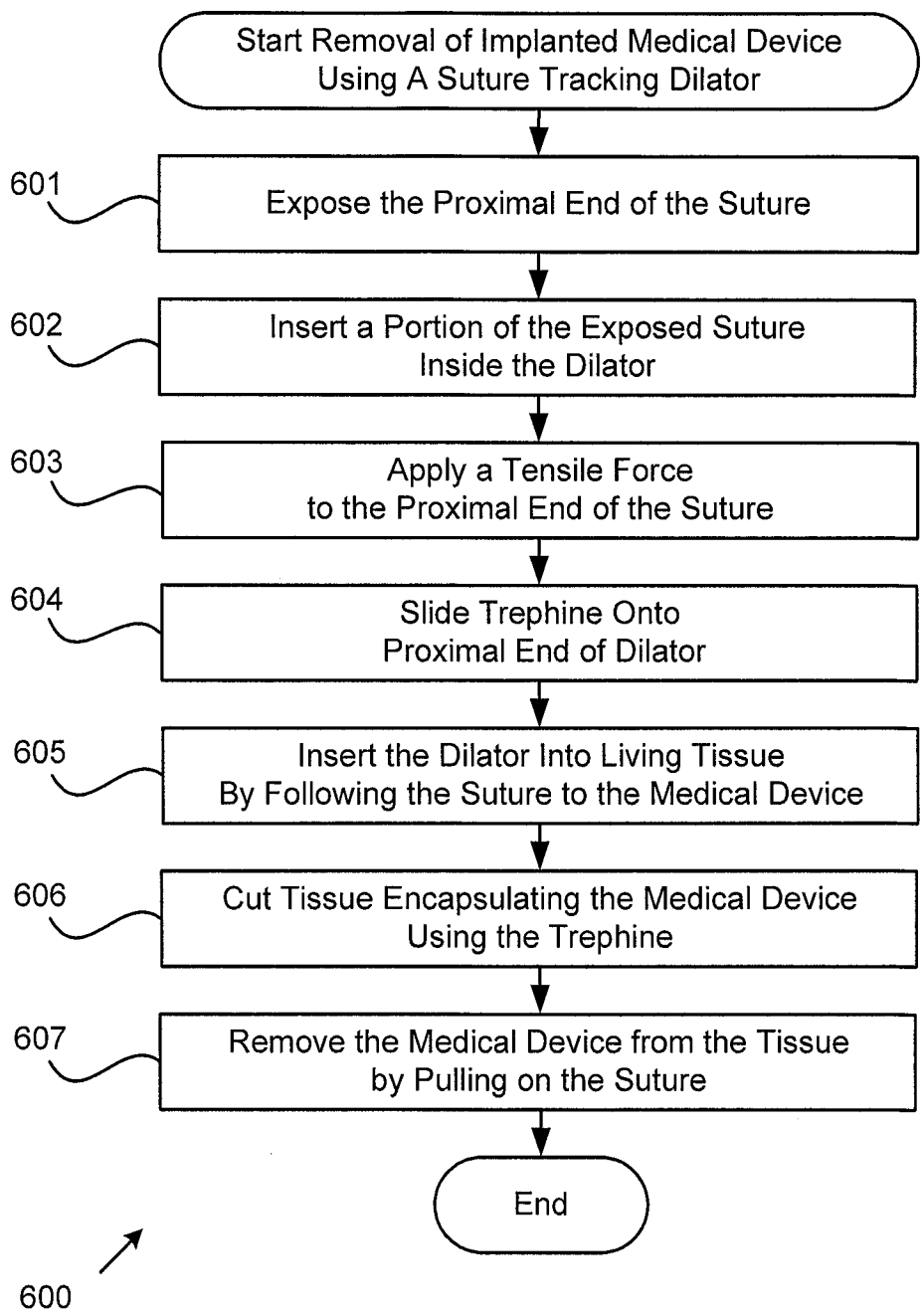
FIG. 6 is a block diagram of a method for removing an implanted medical device using a suture tracking dilator.

FIG. 6 is a block diagram of a method for removing an implanted medical device, such as microdevice 250 using a suture tracking dilator, such as dilator 310 or 510 and parts of this procedure have been discussed with regard to some of the previously described figures. In block 601, the proximal or free end of excess suture 241 of suture 240 is exposed in a surgical procedure, as shown in FIG. 2B. The length of the exposed suture should be longer than the length of the suture tracking dilator. In block 602, a portion of the exposed suture 240 is inserted into the interior of dilator 310 via slit 300, as shown in FIG. 3A, with enough of the suture 240 extending from the proximal end 312 of dilator 310 to enable an operator to be able to hold it with their fingers. In block 603, a tensile force is applied to the proximal end of suture 240 to prevent the suture 240 from falling out of dilator 310. In block 604, a trephine 100 is slid onto dilator 310 as shown in FIG. 3B. In block 605, the distal end 311 of dilator 310 is inserted into living tissue 280, as shown in FIG. 4A. In block 606, trephine 100 is rotated to cut the tissue encapsulating microdevice 250, especially the tissue around eyelet 260, as shown in FIG. 4B. In block 607, the microdevice is removed from the tissue by pulling on the suture. Removing the microdevice can also include removing the dilator and trephine at the same time.

The examples set forth above are provided to give those of ordinary skill in the art a description of how to make and use the embodiments of the suture tracking dilator for microdevice removal, and are not intended to limit the scope of what the inventors regard as their invention. Modifications of the above described dilators and methods for use for carrying out the present invention may be used by persons of skill in the art, and are intended to be within the scope of the following claims. All patents and publications mentioned in the specification may be indicative of the levels of skill of those skilled in the art to which the present invention pertains.

It is to be understood that the present invention is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the present invention pertains.

A number of embodiments of the present invention have been described. Nevertheless, it will be understood that various modifications may be made without departing from the spirit and scope of the present invention. Accordingly, other embodiments are within the scope of the following claims.

We claim:

1. A surgical apparatus comprising:
   a dilator, the dilator comprising:
      a cylindrical tube having a hollow core, a distal end and a proximal end;
      a tubular portion having a distal end, a proximal end and a major radius;
      a conical portion having a distal end, a proximal end and a circular lateral cross section with a radius increasing from a minor radius at the distal end to a major radius at the proximal end, the proximal end of the conical portion coupled with the tubular portion; and
      a slit extending through the dilator from the distal end of the dilator to the proximal end of the dilator; wherein the slit defines a continuous longitudinal opening of fixed width into the hollow core of the dilator; and
   a handle having a proximal end, a distal end with a first fitting and a locking mechanism for releasably fastening the handle to the dilator, the handle configured to slide over the tubular portion when not fastened to the dilator.

2. The apparatus of claim 1, wherein the slit comprises a plurality of substantially straight portions extending across an axial dimension of the dilator, and at least one curved portion, the curved portion being curved along a lateral dimension of the dilator.

3. The apparatus of claim 2, wherein the at least one curved portion is located in the tubular portion.

4. The apparatus of claim 2, wherein the at least one curved portion of the slit is at an acute angle with respect to the axial center line of the dilator.

5. The apparatus of claim 1, further comprising a trephine having a proximal end with a second fitting for releasably coupling to the first fitting of the handle and a distal end with a cylindrical blade.

6. A surgical apparatus comprising:
   a dilator, the dilator comprising:
      a cylindrical tube having a hollow core, a distal end and a proximal end;
      a tubular portion having a distal end, a proximal end and a major radius;
      a conical portion having a distal end, a proximal end and a circular lateral cross section with a radius increasing from a minor radius at the distal end to a major radius at the proximal end, the proximal end of the conical portion coupled with the tubular portion; and
      a slit extending through the dilator from the distal end of the dilator to the proximal end of the dilator; wherein the slit defines a continuous longitudinal opening of fixed width into the hollow core of the dilator; and
   a trephine with a handle and a locking mechanism for releasably fastening the trephine to the dilator; the trephine configured to slide over the tubular portion when not fastened to the dilator.

7. The apparatus of claim 6, wherein the slit comprises a plurality of substantially straight portions extending across an axial dimension of the dilator, and at least one curved portion, the curved portion being curved along a lateral dimension of the dilator.

8. The apparatus of claim 7, wherein the at least one curved portion is located in the tubular portion.

9. The apparatus of claim 7, wherein the at least one curved portion of the slit is at an acute angle with respect to the axial center line of the dilator.

10. A surgical apparatus comprising:
    a dilator, the dilator comprising:
       a cylindrical tube having a hollow core, a distal end a proximal end;
       a tubular portion having a distal end, a proximal end and a major radius;
       a conical portion having a distal end, a proximal end and a circular lateral cross section with a radius increasing from a minor radius at the distal end to a major radius at the proximal end, the proximal end of the conical portion coupled with the tubular portion; and
       a slit extending through the dilator from the distal end of the dilator to the proximal end of the dilator; wherein the slit defines a continuous longitudinal opening of fixed width into the hollow core of the dilator; and
    a medical device configured to be implanted in and withdrawn from living tissue, the medical device comprising:
       an eyelet at one end thereof; and
       a suture attached to the eyelet, a portion of the suture configured to pass through the slit of the dilator and be located within the interior of the dilator during withdrawal of the medical device from the living tissue.

11. The apparatus of claim 10, wherein the suture us a non-absorbable suture.

12. The apparatus of claim 10, wherein the suture is a radio opaque suture.

13. The apparatus of claim 10, wherein the medical device is: a microstimulator, a microsensor or a combination microstimulator and microsensor.

14. The apparatus of claim 10, wherein the slit comprises a plurality of substantially straight portions extending across an axial dimension of the dilator, and at least one curved portion, the curved portion being curved along a lateral dimension of the dilator.

15. The apparatus of claim 14, wherein the at least one curved portion is located in the tubular portion.

16. The apparatus of claim 14, wherein the at least one curved portion of the slit is at an acute angle with respect to the axial center line of the dilator.

17. An apparatus comprising: a dilator, the dilator comprising: a cylindrical tube having a hollow core, a distal end and a proximal end; a tubular portion having a distal end, a proximal end and a major radius; a conical portion having a distal end, a proximal end a circular lateral cross section with radius increasing from a minor radius at the distal end to a major radius at the proximal end, the proximal end of the conical portion coupled with the tubular portion; and a slit extending through the dilator from the distal end of the dilator to the proximal end of the dilator; wherein the slit defines a continuous longitudinal opening of the fixed width into the hollow core of the dilator; a suture attached to a medical device, a portion of the suture configured to pass through the slit of the dilator and be located within the interior of the dilator during withdrawal of the medical device from the living tissue.

18. The apparatus of claim 17, wherein the slit comprises a plurality of substantially straight portions extending across an axial dimension of the dilator, and at least one curved portion, the curved portion being curved along a lateral dimension of the dilator.

19. The apparatus of claim 18, wherein the at least one curved portion is located in the tubular portion.

20. The apparatus of claim 18, wherein the at least one curved portion of the slit is at an acute angle with respect to the axial center line of the dilator.

21. A method for removing a medical device implanted in living tissue, the medical device comprising a suture attached thereto, the method comprising:
    exposing the proximal end of the suture;
    inserting a portion of the exposed suture inside a dilator, the suture passing through the interior portion of the dilator; the dilator comprising:
       a cylindrical tube having a hollow core, a distal end and a proximal end;
       a tubular portion having a distal end, a proximal end and a major radius;
       a conical portion having a distal end, a proximal end and a circular lateral cross section with a radius increasing from a manor radius at the distal end to a major radius at the proximal end, the proximal end of the conical portion coupled with the tubular portion; and
       a slit extending through the dilator from the distal end of the dilator to the proximal end of the dilator; wherein the slit defines a continuous longitudinal opening of fixed width into the hollow core of the dilator;
    applying a tensile force to the proximal end of the suture;
    sliding a trephine onto the proximal end of the dilator;
    inserting the dilator into the living tissue by following the suture up to the implanted medical device;
    cutting tissue encapsulating the implanted device using the trephine; and
    removing the implanted device by pulling on the suture.

22. The method of claim 21, wherein the suture is a non-absorbable suture.

23. The method of claim 21, wherein the suture is a radio opaque suture.

24. The method of claim 21, wherein removing the implanted device further comprises withdrawing the trephine from the living tissue when removing the implanted medical device.

* * * * *

UNITED STATES PATENT AND TRADEMARK OFFICE
CERTIFICATE OF CORRECTION

PATENT NO. : 9,623,220 B2  
APPLICATION NO. : 14/207404  
DATED : April 18, 2017  
INVENTOR(S) : Perrin et al.

Page 1 of 1

It is certified that error appears in the above-identified patent and that said Letters Patent is hereby corrected as shown below:

On the Title Page

Item [71] to read as follows:  
[71] Applicant: The Alfred E. Mann Foundation For Scientific Research Signed and Sealed this  
Twenty-first Day of November, 2017

Joseph Matal  
*Performing the Functions and Duties of the*  
*Under Secretary of Commerce for Intellectual Property and*  
*Director of the United States Patent and Trademark Office*